United States Patent [19]

Cheng et al.

[11] Patent Number: 5,670,115
[45] Date of Patent: Sep. 23, 1997

[54] HYDROGEN SENSOR

[75] Inventors: Yang-Tse Cheng, Rochester Hills; Yang Li, Troy; Daniel John Lisi, Eastpointe, all of Mich.; Stanley Gutowski, Pittsford, N.Y.; Andrea A. Poli, St. Clair Shores, Mich.

[73] Assignee: General Motors Corporation, Detroit, Mich.

[21] Appl. No.: 543,541

[22] Filed: Oct. 16, 1995

[51] Int. Cl.[6] .................................. G01N 27/04
[52] U.S. Cl. ........................ 422/90; 422/83; 422/94; 422/95; 422/96; 422/97; 204/290 R; 204/291; 204/293; 204/419; 429/218; 429/223
[58] Field of Search ................ 422/83, 90, 94, 422/95, 96, 97; 204/290 R, 291, 293, 419; 429/218, 223

[56] References Cited

U.S. PATENT DOCUMENTS

| | | | |
|---|---|---|---|
| 4,030,340 | 6/1977 | Chang | 73/23 |
| 4,244,918 | 1/1981 | Yasuda et al. | 422/95 |
| 4,324,760 | 4/1982 | Harris | 422/98 |
| 4,324,761 | 4/1982 | Harris | 422/98 |
| 4,453,397 | 6/1984 | Ohta et al. | 73/23 |
| 4,728,586 | 3/1988 | Venkatesan et al. | 429/94 |
| 4,892,834 | 1/1990 | Rauh | 436/149 |
| 4,946,646 | 8/1990 | Gamo et al. | 420/415 |
| 5,084,154 | 1/1992 | Wakizoe et al. | 204/290 R |
| 5,096,667 | 3/1992 | Fetcenko | 420/580 |
| 5,278,001 | 1/1994 | Ono et al. | 429/101 |
| 5,367,283 | 11/1994 | Lauf et al. | 338/34 |
| 5,427,672 | 6/1995 | Bocker et al. | 204/426 |
| 5,490,970 | 2/1996 | Gamo et al. | 420/424 |
| 5,525,435 | 6/1996 | Pourarian | 429/218 |

FOREIGN PATENT DOCUMENTS 0194347 10/1985 Japan.

OTHER PUBLICATIONS

Cheng et al, "Preparation and Characterization of Pd/Ni Thin Films for Hydrogen Sensing," *Sensors and Actuators* B 99 (1995) 1-999, pp. 1-6.
Grossman et al, "Hydrogen Leak Detection Technology," Florida Institute of Technology, Progress Report #4 to NASA— J. F. Kennedy Space Center, Oct. 10, 1993.
Hughes et al, "Thin Films of Pd/Ni Alloys for Detection of High Hydrogen Concentrations," *Journal of Applied Physics*, vol. 71, No. 1, 1 Jan. 1992, pp. 542-544.

*Primary Examiner*—Jill Warden
*Assistant Examiner*—Sharidan Carrillo
*Attorney, Agent, or Firm*—George A. Grove

[57] ABSTRACT

A sensor for hydrogen is disclosed comprising an electrically insulating substrate carrying a thin amorphous film of co-deposited nickel and zirconium and an overlying film of palladium wherein during the operation of the sensor, hydrogen in a sample gas is dissociated on the palladium film and diffuses into the nickel-zirconium film to change its electrical resistance in proportion to the amount of hydrogen in the sample to be analyzed.

8 Claims, 3 Drawing Sheets

HYDROGEN SENSOR

This invention pertains to devices for sensing or detecting hydrogen, especially hydrogen in a gaseous mixture. More specifically, this invention is a hydrogen sensor that is selective to hydrogen in mixtures, provides a fast response time in detecting hydrogen over a substantial range of hydrogen concentrations, and retains its utility at gas temperatures ranging from ambient to at least 150° C.

BACKGROUND OF THE INVENTION

Hydrogen is a commonly used element, and the timely and accurate measurement of its concentration in a gaseous mixture is a challenging problem. The uses of hydrogen sensors include the detection of leaks in hydrogen fueled rocket motors and the detection or measurement of hydrogen in semiconductor fabrication operations and in battery manufacturing and testing. Hydrogen sensors are also required in the operation of hydrogen-oxygen fuel cell devices and engines. It is in this latter application that there is a particular need for hydrogen sensors that have a fast response time to varying hydrogen concentrations in mixtures with nitrogen, carbon dioxide and water vapor and which are operable and effective at temperatures of the order of 100° C. In broader perspective, the development of a highly useful hydrogen sensor requires that it possess attributes such as chemical selectivity, reversibility, fast response, sensitivity, durability, small size, ease of fabrication, simple control system and resistance to contamination and poisoning.

Thin films of palladium and palladium alloys have been used for hydrogen detection. Examples of such palladium alloys are palladium nickel and palladium silver alloys. The electrical resistance of such palladium or palladium alloy thin films is a function of the absorbed hydrogen content, and this variation in electrical resistance when exposed to $H_2$-containing gas provides the basis for hydrogen content measurement. However, the response times of such palladium and palladium alloy thin film hydrogen sensors to the $H_2$-containing gas have been quite slow. Further, they often fail to operate at temperatures of the order of 100° C. Accordingly, such thin film Pd devices have limited or no applicability in applications such as the management of fuel cells which require a fast response time at such elevated temperatures.

SUMMARY OF THE INVENTION

This invention provides a thin film hydrogen-sensing device that is effective at temperatures from normal room temperature to at least 150° C. Furthermore, it provides a fast response time of less than 10 seconds for hydrogen over a broad composition range, for example, between 0.1 and 50 percent by volume. It relies on a thin Pd film to catalyze dissociation of the $H_2$ molecule and utilizes a film of amorphous NiZr for hydrogen content measurement.

The device in its simplest, single element form comprises an electrically insulating substrate that is durable over the intended operating temperature range of the device and is inert to hydrogen gas and other gases that may be present. Alumina is preferred for this purpose. Any suitable electrically resistive materials such as oxidized silicon or the like may be used. Co-deposited as an amorphous film on a surface of the alumina body is an intimate mixture of nickel and zirconium in accordance with the formula $Ni_xZr_{100-x}$ where $25 \leq x \leq 75$. A thin film of palladium metal is then applied to overlie the amorphous nickel-zirconium film.

In the operation of the device, the palladium film serves to dissociate hydrogen molecules at the Pd surface, and the hydrogen atoms diffuse into the palladium film. Hydrogen atoms diffuse through the thin palladium film into the underlying nickel-zirconium film and dissolve therein. The flow of hydrogen atoms into and out of the respective films is reversible depending upon the $H_2$ content of the ambient gas. The electrical resistivity of the nickel-zirconium film increases as the content of dissolved hydrogen increases. The effect on the electrical resistivity of such film is proportional to the hydrogen content over a wide range of temperatures, and this property of the films provides the operating basis of the sensor. In addition to catalyzing the dissociation of hydrogen molecules from the ambient atmosphere and absorbing hydrogen atoms, the palladium film also serves as a barrier to oxidation of the underlying nickel-zirconium film. Suitable electrical contacts are made at opposite edges of the nickel-zirconium film to accommodate a measurement of its electrical resistance.

The palladium film is quite thin, suitably of the order of 5 to 50 nanometers and preferably 5 to 15 nanometers. The palladium layer needs only to be thick enough to fully cover the surface of the underlying nickel-zirconium alloy and to provide a continuous oxidation barrier as well as a continuous catalyst surface for the dissociation of hydrogen. The thickness of the amorphous nickel-zirconium alloy film is greater than that of the palladium layer. It needs to be thick enough to provide a continuous electrical resistance path over the surface of the underlying substrate material and to serve as the principal conductivity path for the sensor operation. Preferably, the cross-sectional area of the nickel-zirconium film for electrical conduction is at least ten times the cross-sectional area for electrical conduction of the palladium film layer. The substrate provides the structural support and the operating surface for the sensor device. The thickness of the nickel-zirconium fill is suitably in the range of 20 nanometers up to a few micrometers. However, it is to be recognized that the thicker the layer, the longer the time that it takes its hydrogen content to become representative of the atmosphere being measured.

Thus, when the hydrogen content of the atmosphere that contacts the palladium layer increases or decreases, more or less hydrogen flows into or out of the palladium film and underlying nickel-zirconium fill. Operated at temperatures about 90° C. the response time of the subject device is considerably faster than that of the prior art palladium and palladium alloy resistance films. At temperatures of the order of 90° C. response times for the subject device are typically less than 10 seconds for gases containing hydrogen over a broad composition range between about 0.1 and 50 percent by volume.

While the invention has been described in terms of a brief summary, other objects and advantages of the invention will become more apparent from a detailed description thereof which follows. Reference will be had to the drawings.

DESCRIPTION OF PREFERRED EMBODIMENTS

Single element test sensors of the subject invention were prepared. Flat rectangular plates of alumina were used as the substrate. The dimensions of the plates were 12 mm long by 5 mm wide by 2 mm thick. The films of nickel-zirconium alloy and of palladium were applied to a full major surface of the plates by electron beam evaporation in ultra-high vacuum. However, the film layers in the sensors of this invention may be prepared by other known practices such as sputtering, plating or by separately forming the films and bonding them to the substrate. Oxidized silicon substrates have also been used.

High purity (greater than 99.8 percent) sources of zirconium and nickel were employed to form the NiZr films on the $Al_2O_3$ substrates. Zirconium and nickel were simultaneously evaporated from two electron beam evaporation sources onto the alumina substrates at 30° C. and all in a high vacuum chamber. The deposition rate of each material was controlled by an Inficon XTC monitor. Deposition was controlled to produce a film on each substrate that was about 50 nanometers thick. The rates were controlled such that the desired composition in the deposited film was achieved. Immediately after depositing a specified nickel-zirconium layer, a palladium layer of about 15 nanometers thick was deposited from a palladium (99.8 percent pure) electron beam evaporation source onto the nickel-zirconium layer in the same ultra-high vacuum chamber. The base pressure in the chamber was in the $10^{-9}$ torr range, and the pressure during deposition was in the $10^{-8}$ torr range. The low pressure during deposition ensures the high purity of the films for the test samples. The composition and mass thickness of the films were also determined quantitatively by electron probe microanalysis. The film structure was studied by x-ray diffraction with $CuK_\alpha$ radiation. The composition, depth profile and film purity were examined by x-ray photoelectron spectroscopy with argon ion sputtering. Thus, the composition and characteristics of the films were well known.

Figure 1:
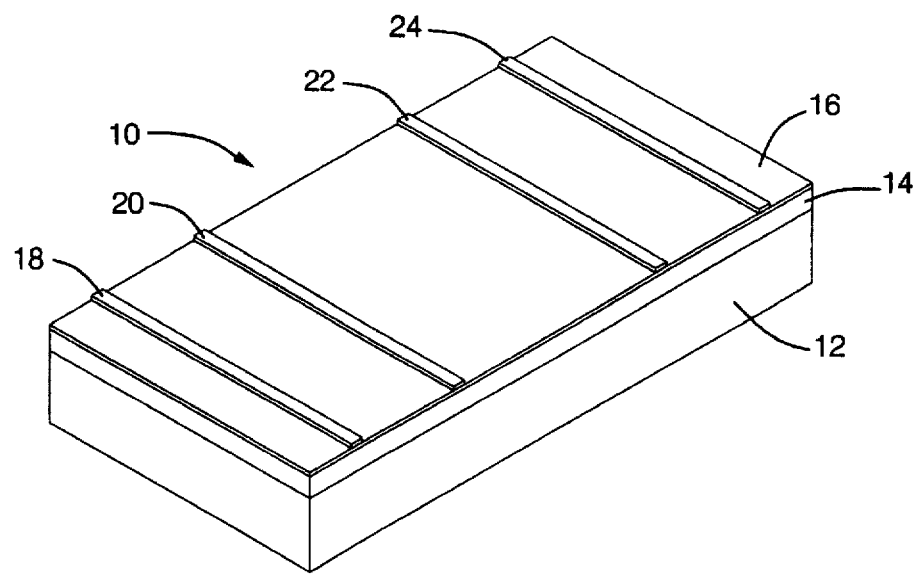
FIG. 1 is a perspective view partly broken away and in cross section showing the component layers of the single element embodiment of the hydrogen sensing device of this invention.

FIG. 1 illustrates a single resistor element embodiment of a subject hydrogen sensor in perspective view partly broken away and in cross section. The sensor 10 comprises an alumina (or oxidized silicon or the like) structural, film-carrying substrate plate 12. The nickel-zirconium alloy film is depicted at 14 and the overlying palladium layer at 16. Obviously, the thickness of each layer is exaggerated for the purpose of illustration. Four platinum electrical contacts 18, 20, 22 and 24 were bonded to the palladium film 16 of the device. They were bonded to layer 16 by an electrically-conductive silver-filled polyimide adhesive (not shown) which was cured at 175° C. in air for one hour.

The nickel-zirconium alloy film 14 was deposited as an amorphous film in the test samples. The palladium overlayer 16 was crystalline. It was determined that nickel-zirconium alloys of approximately equal atomic proportions of each constituent (e.g., $Ni_xZr_{100-x}$ where $45 \leq x \leq 55$) provide a very effective and versatile sensor, especially if the concentration of hydrogen in the gas to be analyzed is likely to vary over a range, for example, from 0.1 to 50 percent by volume.

In the event that the sensor will be used in a relatively high hydrogen content gas, then the nickel content of the nickel-zirconium amorphous film is advantageously greater than 50 atomic percent, approaching the upper limit of about 75 atomic percent. Conversely, if the hydrogen content of the gas to be analyzed is known to be low, then the zirconium content of the amorphous alloy film can exceed 50 percent and approach its upper limit of about 75 atomic percent. As stated above, suitably, the composition of the nickel-zirconium layer is in the range of $Ni_xZr_{100-x}$ where x lies between about 25 and 75 atomic percent.

The single element test samples 10 whose performance will be described in the following portion of the specification had a nickel-zirconium film composition of $Ni_{52}Zr_{48}$. A 50 nanometer thick $Ni_{52}Zr_{48}$ film with a 15 nanometer overlying layer of palladium, both thicknesses as determined by electron probe microanalysis, were found to have very high performance characteristics in the test gas and temperature examples as described in this specification. X-ray diffraction analysis showed that the diffraction peaks belonged to either the alumina substrate or the palladium thin film. The absence of sharp diffraction peaks from the nickel-zirconium layer indicates that that layer was amorphous. The sputter depth profile of the as-deposited nickel-zirconium film 14 indicated that the oxygen impurity was less than 5 atomic percent. It also showed that the palladium film 16 covered the nickel-zirconium film and that the compositions of the respective films were uniform throughout their respective depths.

$Pd/Ni_{52}Zr_{48}$-alumina sensors 10 prepared as described above were individually tested in a computer controlled system. Very high purity sources of nitrogen, hydrogen, carbon dioxide and carbon monoxide were employed to make up various gaseous atmospheres of known composition for the tests. Such prepared atmospheres were caused to flow over the respective test sensors through a 55 cm long, 2.45 cm diameter quartz tube. A major part of the tube except for the inlet and outlet were enclosed in a cylindrical furnace. The compositions of the flowing synthetic gas mixtures were controlled by flow controllers which admitted one or more of the gases through a manifold into the entrance to the quartz tube flow channel. The sensor was positioned two centimeters downstream from the point where the tube emerged from the furnace. Most of the interior of the tube upstream of sensor 10 was filled with quartz beads to increase heat transfer to the flowing gas. The temperature of the gas and sensor was measured using a thermocouple adjacent the sensor element. For all measurements, the total pressure of the hydrogen-containing gas was maintained just above atmospheric pressure. The total flow rate was two standard liters per minute. The electrical resistance of the sensor film was determined by four probe (i.e., elements 18, 20, 22 and 24) DC conductivity measurements using an HP6181C DC current source and an HP3478A multimeter. A constant current of 1mA was conducted through contacts 18 and 24 during all of the measurements. The voltage drop was measured across contacts 20 and 22. The flow controllers and the voltmeter were interfaced with a personal computer. In the construction of FIG. 1, the thickness of NiZr layer 14 was substantially greater than Pd layer 16. Thus, although contacts 18, 20, 22 and 24 were attached to Pd layer 16, the major current flow was through NiZr layer 14, and the voltage drop across contacts 20 and 22 reflects the electrical resistance of layer 14.

The effect of water vapor in the test gas on the test sensor was studied by injecting liquid water into the two SLPM gas flow upstream from the heated furnace at a rate of 18 ml per hour using a minipump.

The response time of the test sensor was studied using a differentially pumped mass spectrometer (UTI 100C) which monitored the gas composition near the sensor position. Of course, changes in the $H_2$ content of the synthetic test atmospheres were made at the manifold well upstream of the flow channel and sensor 10. The hydrogen signal from the mass spectrometer was recorded as a function of time at 90° C. for several known concentrations. The measured time constant for hydrogen concentration at sensor 10 to rise or fall to 90 percent of specified value was about six seconds. Considering the tubing length between the sensor and the offset mass spectrometer, the actual time constant for hydrogen concentration to rise and fall at the sensor location must have been shorter than six seconds.

EXAMPLE 1

5% Hydrogen in Nitrogen at 90° C.

Figure 2:
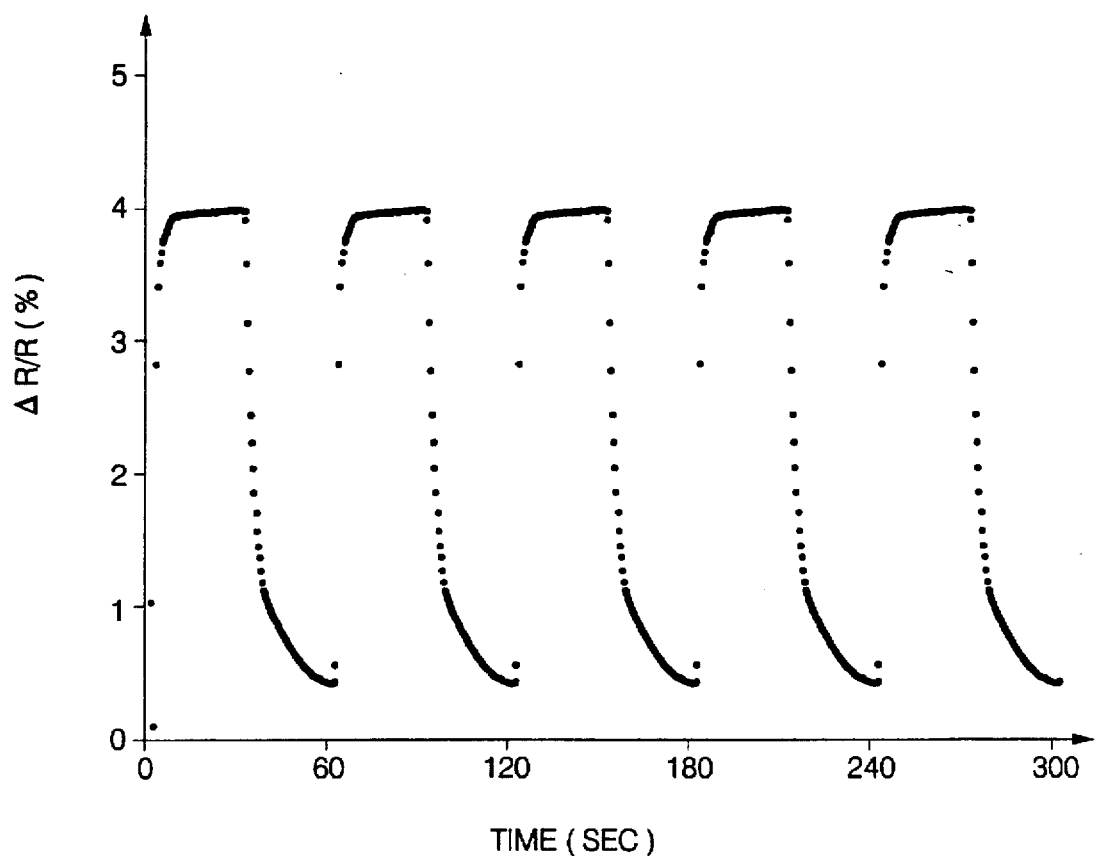
FIG. 2 is a plot of percentage change in electrical resistance, $\Delta R/R_0$, as a $Pd/Ni_{52}Zr_{48}$ thin film is cycled between pure $N_2$ and 5% $H_2$ balanced with $N_2$, at 90° C.

The proportional change in resistance of the NiZr layer 14, $\Delta R/R_0$ equals $(R-R_0)/R_0$, where Ro is the resistance of the film layer in 100% $N_2$ before introducing hydrogen, was obtained during cycling the test sensor films between pure nitrogen and nitrogen containing hydrogen in amounts from 0.1 to 50 percent by volume hydrogen at 90° C. A typical cycling result for a palladium/$Ni_{52}Zr_{48}$ thin film is shown in FIG. 2. FIG. 2 shows the percentage change in resistance, $\Delta R/R_0 \times 100$, as a test sensor 10 is cycled between pure nitrogen and 5% hydrogen balanced with nitrogen at 90° C. When hydrogen is turned on to produce the $N_2$-$H_2$ mixture, $\Delta R/R_0$ increases with time and quickly reaches a steady state value for a given hydrogen concentration. When hydrogen is turned off, $\Delta R/R_0$ quickly decreases with time. Thus, the sensor output is seen to be reversible as the hydrogen content of the test gas increases and decreases.

The response time, defined as the time duration to reach 90 percent of the final change in $\Delta R/R_0$, was about four seconds when hydrogen was turned on. When hydrogen was turned off, the time for a 90 percent resistance decrease was longer. The same characteristics apply to the prior art palladium and Pd alloy sensors except that in both instances of $H_2$ increase and decrease, the total response time is significantly longer.

EXAMPLE 2

Various $H_2$-$N_2$ Mixtures at 90° C.

Figure 3:
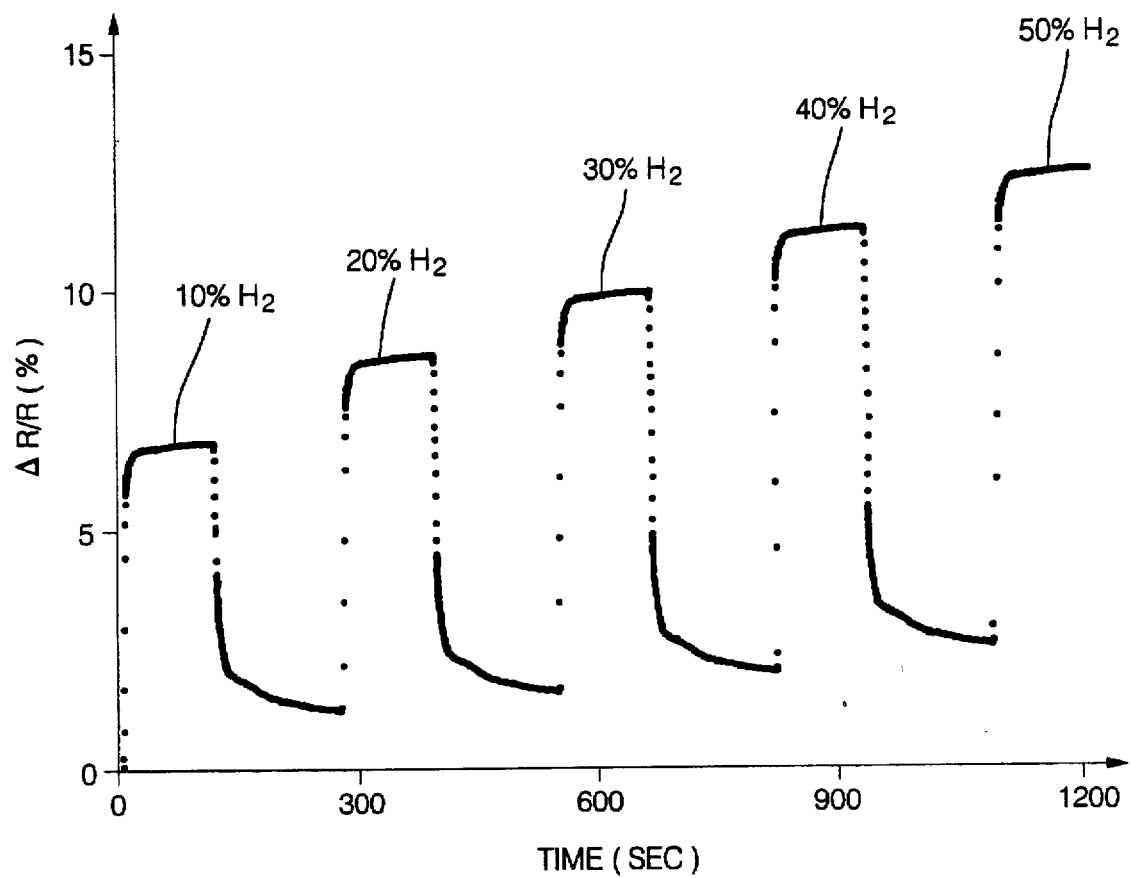
FIG. 3 is a plot of percentage change in electrical resistance, $\Delta R/R_0$, as a thin film is cycled between pure $N_2$ and 10, 20, 30, 40 or 50 percent $H_2$ balanced with $N_2$, at 90° C.

The sensor response was also studied as a function of hydrogen concentrations of 10%, 20%, 30%, 40% and 50%, balance nitrogen (see FIG. 3). Again, $\Delta R/R_0(\%)$ is plotted versus time as hydrogen in increasing amounts was intermittently added to nitrogen. Clearly, the subject sensor as depicted at 10 in FIG. 1 can detect hydrogen over this wide concentration range without saturation of the sensor. The response time is less than six seconds and seems independent of hydrogen concentration, all at temperatures of 90° C.

Hydrogen-Carbon Dioxide Atmospheres

The response of the palladium/$Ni_{52}Zr_{48}$ sensor to hydrogen in mixtures with pure carbon dioxide was measured. Similar to the results of hydrogen-nitrogen mixtures, the sensor had a quick response (less than six seconds) when the hydrogen concentration was varied between one percent and 50 percent by volume at 90° C. The effect of water vapor in the nitrogen-carbon dioxide mixture was then studied by injecting water into the gas stream. The concentration of water was estimated to be about 20 percent by volume by measuring the volume of condensed water downstream from the sensor position. It was determined that the sensor rapidly detected hydrogen in the presence of carbon dioxide and water over the composition range between 5 percent and 50 percent. This observation was expected because neither water nor carbon dioxide react with hydrogen on the surface of palladium at 90° C.

The Effect of Carbon Monoxide on the Palladium/$Ni_{52}Zr_{48}$ Sensor at 90° C.

It is known that carbon monoxide can poison a palladium/nickel alloy thin film sensor at 25° C. by blocking palladium surface sites. This significantly increases a sensor response time because it takes much longer for hydrogen to dissociate and diffuse into the alloy. In the test with the subject sensor to a gas containing 0.1 percent by volume carbon monoxide and 1 percent hydrogen balanced with carbon dioxide, it was observed that the sensor response time was longer when carbon monoxide and hydrogen were both present. In this instance, at 90° C. the response time was about 20 seconds. Thus, carbon monoxide can degrade the performance of the subject sensor when hydrogen and carbon monoxide are both present. However, the carbon monoxide poisoning effect at 90° C. is much smaller than at 25° C. and is much less than with the prior art palladium alloy sensors. The observation is that such sensors lose most of their sensitivity at 90° C. and above.

In the sensors of this invention, it is preferred that the top film layer (e.g., 16 in FIG. 1) be substantially pure palladium, although many palladium alloys will work. The reason for the use of substantially pure palladium films as the top layer is that the dissociation kinetics of hydrogen molecules on the surface of palladium is faster than that on most other metal surfaces. Second, hydrogen atoms readily diffuse through the palladium film into the $Ni_xZr_{100-x}$ layer. Third, the palladium film serves to prevent oxidation of the nickel-zirconium layer by blocking oxygen diffusion from the ambient into the nickel-zirconium films. The thickness of the nickel-zirconium layer is preferably substantially greater than that of the palladium so that the palladium does not electrically short out the NiZr layer. In operation of the subject sensor, the electrical resistance change is mainly caused by the change in the electrical properties of the nickel-zirconium film due to the presence and amount of absorbed hydrogen atoms.

As demonstrated above, a useful hydrogen sensor may be made having only a single palladium/$Ni_xZr_{100-x}$ resistive element on the electrically insulating substrate. However, such a single resistive element sensor usually is preferable only when the temperature of the gas to be analyzed is known and does not vary appreciably. This limitation arises because $Ni_xZr_{100-x}$ films have a small but finite temperature coefficient of electrical resistance (TCR). For this reason, a more versatile device comprises at least two resistor elements connected in a parallel relationship construction on the electrically insulating substrate. Such a device is illustrated in FIGS. 4 and 5.

Figure 4:
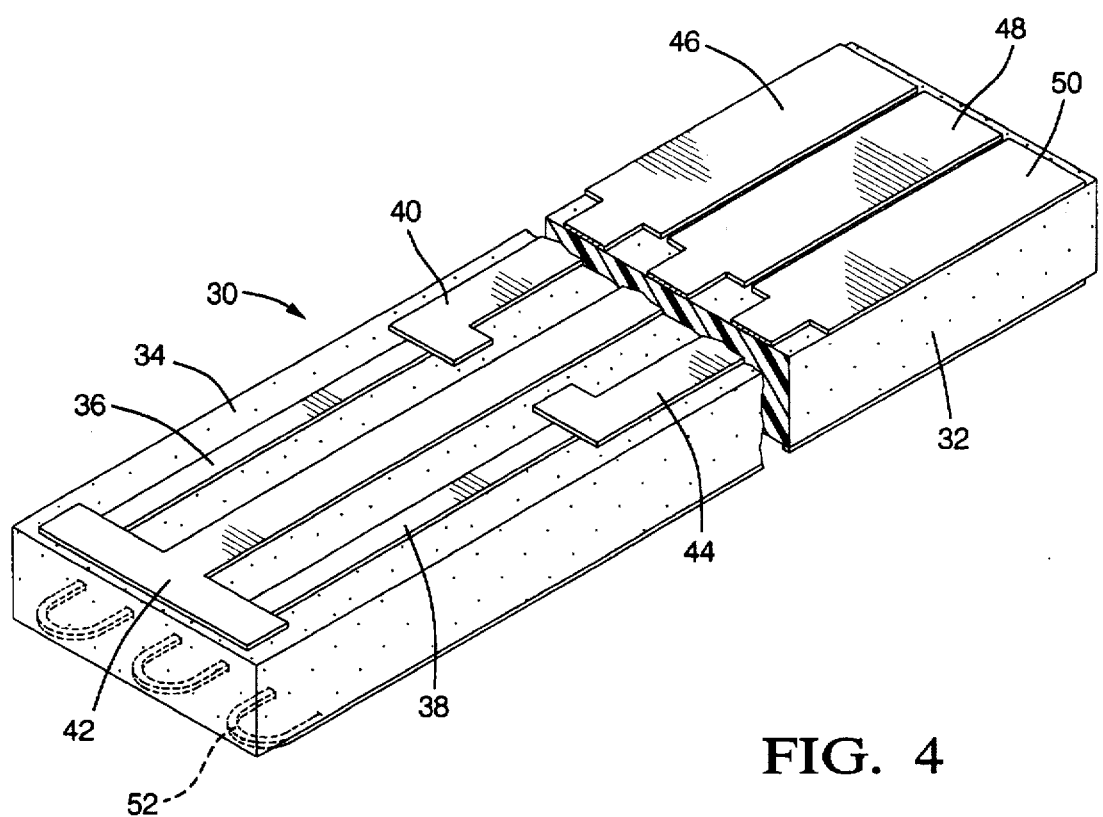
FIG. 4 is a perspective view showing the top and sensor element bearing surface of a heated two element embodiment of the hydrogen-sensing device of this invention.
Figure 5:
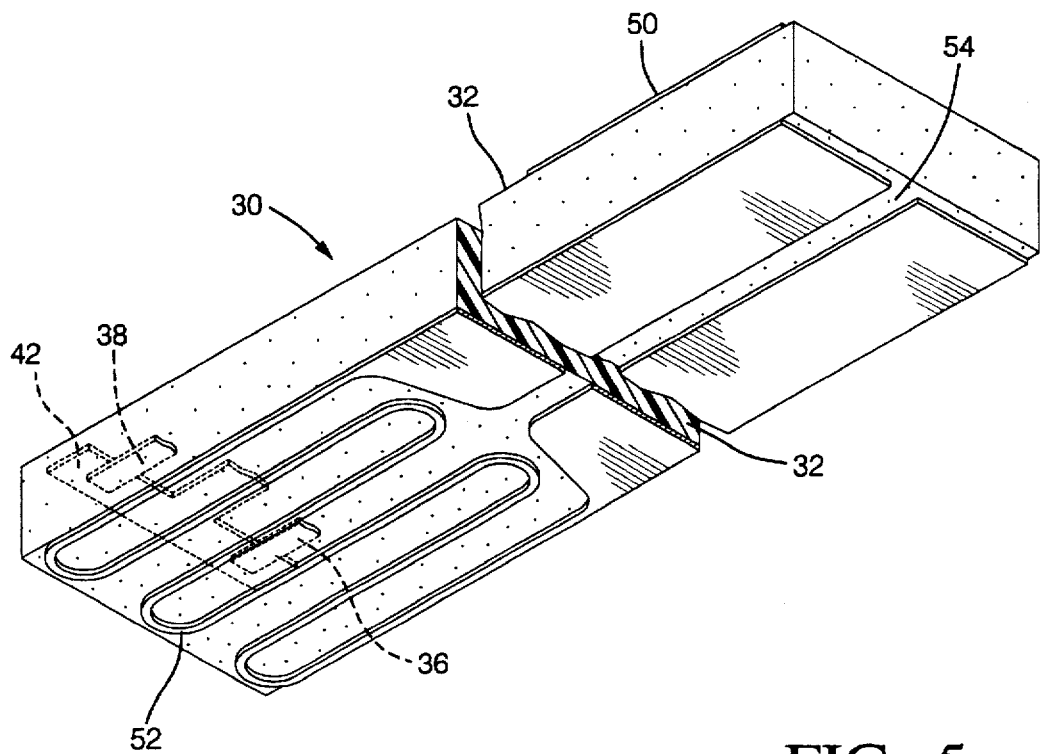
FIG. 5 is a perspective view showing the bottom, heater element bearing surface of the hydrogen-sensing device of FIG. 4.

Referring to FIGS. 4 and 5, two element sensor 30 comprises an electrically nonconductive substrate 32 that is inert to hydrogen and other constituents of the sample gas. Alpha alumina is a preferred substrate material because it is relatively inexpensive, it can be formed into durable substrate bodies, and it is an inert insulator material. Other materials with like properties are suitable. Deposited on the upper surface 34 of substrate 32 is a hydrogen sensor element 36. Hydrogen sensor element 36 consists of two metal film layers as described with respect to sensor 10 in FIG. 1.

In this embodiment, the $Ni_xZr_{100-x}$ layer and overlying Pd film (collectively element 36) are deposited only on a small region of the large substrate 32. Closely adjacent to $H_2$ sensor element 36 is a temperature sensor or compensator resistive element 38. Thick film metallization layers 40, 42 and 44 provide electrical leads and interconnections to the sensor element 36 and compensator element 38. It is seen that leads 40 and 42 respectively connect to ends of $H_2$ sensor 36 and leads 42 and 44 to ends of temperature sensor/compensator element 38. Terminal pads 46, 48 and 50 are formed at ends of layers 40, 42 and 44, respectively. Electrical connections from external circuitry are made to the terminal pads to provide a suitable current through the elements 36 and 38 and to monitor the voltage across them as described with respect to the one element sensor 10 in FIG. 1. Of course, such external connections may include additional resistors in a bridge arrangement as depicted, for example, in U.S. Pat. No. 5,367,283 to Lauf et al, or such other additional circuitry as a user may wish to employ.

Temperature sensor/compensator element 38 is employed to balance or permit correction for the TCR of the Pd/NiZr film of $H_2$ sensor element 36. In one embodiment of this two resistive element device, the resistive films in each element 36, 38 are identical $Ni_xZr_{100-x}$ resistance films. In the resistive element 36 that is to serve as the hydrogen detector, the upper film is preferably pure palladium as described above. On the temperature compensator element 38, a different cover layer such as an oxide of Al, Si or Ti is used which does not permit hydrogen to diffuse into its underlying nickel-zirconium layer. Thus, in this two element hydrogen sensor/temperature compensator construction, any variation in the temperature of the sensor or the gas being analyzed is compensated for by the parallel resistor construction that experiences the same temperature. Since both resistors consist of substantially the same nickel-zirconium film and only one of the films is affected by the hydrogen content of the gas, the difference in resistances or voltage drops over the films is indicative of the hydrogen content of the gas.

In other embodiments, the temperature compensator element 38 may be a hydrogen non-absorbing metal with appropriate resistance and TCR. This may be achieved, e.g., using Au, Pt or Ni alloy thin films including Ni-rich palladium-nickel alloy thin films of appropriate thickness and composition.

The two element sensor device 30 may include a suitable thin film or thick film heater element 52 on the bottom surface 54 of substrate 32 so that the sensor elements 36 and 38 borne by substrate 32 can both be heated to any desired temperature for the hydrogen detection or sensor measurement. Since the sensor element of this invention remains effective and responsive at temperatures from normal room temperature to 150° C. and hydrogen dissociation and diffusion is faster at elevated temperatures, it may be preferred to maintain the sensor in the 90° C. to 150° C. temperature range even though the gas stream being analyzed is at a lower temperature.

While this invention has been described in terms of certain specific embodiments thereof, it will be appreciated that other forms could readily be adapted by one skilled in the art. Accordingly, the scope of this invention is to be considered limited only by the following claims.

What is claimed is:

1. A sensor for hydrogen comprising:

an electrically insulating substrate that is inert to hydrogen gas, said substrate having a surface adapted to receive thin film metallization, an amorphous metal film on said surface and consisting essentially of co-deposited nickel and zirconium in accordance with $Ni_xZr_{100-x}$ where $25 \leq x \leq 75$, said amorphous film being capable of dissolving hydrogen and having an electrical resistance which varies with said dissolved hydrogen in said film, and a film consisting essentially of palladium overlying said amorphous nickel-zirconium film.

2. A sensor for detecting hydrogen content in a gas sample comprising:

an electrically nonconductive substrate, inert to hydrogen gas and having a surface adapted to receive thin film metallization, an amorphous metal alloy film on said surface and consisting essentially of codeposited nickel and zirconium in accordance with $Ni_xZr_{100-x}$, where $25 \leq x \leq 75$, and a film consisting essentially of palladium overlying the entirety of said nickel and zirconium film, said palladium and nickel-zirconium films being reversibly receptive to hydrogen atoms in proportion to the hydrogen content of said gas and the electrical resistance of said nickel-zirconium film being proportional to the hydrogen content.

3. A sensor for detecting hydrogen content in a gas sample comprising:

an electrically nonconductive substrate, inert to hydrogen gas and having a surface adapted to receive thin film metallization, an amorphous metal alloy film on said surface and consisting essentially of codeposited nickel and zirconium in accordance with $Ni_xZr_{100-x}$, where $25 \leq x \leq 75$, and a film consisting essentially of palladium overlying the entirety of said nickel and zirconium film, said palladium and nickel-zirconium films being reversibly receptive to hydrogen atoms in proportion to the hydrogen content of said gas and the electrical resistance of said nickel-zirconium film being proportional to the hydrogen content, a cross-sectional area of said nickel-zirconium film for electrical conduction being at least ten times greater than a cross-sectional area of a palladium film.

4. A sensor for detecting hydrogen content in a gas sample comprising:

an electrically nonconductive substrate, inert to hydrogen molecules and having a surface for receiving thin film metallization, a thin film sensor element on said surface responsive to the hydrogen content of said gas comprising (a) an amorphous metal film on said substrate and consisting essentially of codeposited nickel and zirconium in accordance with $Ni_xZr_{100-x}$ where $25 \leq x \leq 75$ and (b) a film consisting essentially of palladium metal overlying the entirety of said nickel-zirconium film, and a temperature compensator element on said surface adjacent to said sensor element, said compensator element being nonresponsive to the hydrogen content of said gas.

5. A sensor as recited in any of claims 1 through 4 in which the substrate consists essentially of alpha-alumina.

6. A sensor as recited in any of claims 1 through 4 in which nickel and zirconium in the amorphous film are in the range of $Ni_xZr_{100-x}$ where $45 \leq x \leq 55$.

7. A sensor as recited in claim 4 in which said temperature compensator element is electrically resistive and is connected in parallel electrical current flow relationship with respect to said sensor element.

8. A sensor as recited in claim 4 further comprising a heating element adapted to heat said sensor element and said compensator element to a temperature above a temperature of the gas sample.

* * * * *